United States Patent [19]

Cort et al.

[11] 4,237,119
[45] Dec. 2, 1980

[54] LONG-ACTING OXYTOCIN ANALOGS FOR USE IN INDUCING AND ACCELERATING LABOR IN MAMMALS, PARTICULARLY FARM ANIMALS

[75] Inventors: Joseph H. Cort, Prague; Tomislav Barth, Roztoky u Praha; Karel Jost, Prague; Zdenek Veznik, Brno, all of Czechoslovakia

[73] Assignee: Ceskoslovenska akademie ved, Prague, Czechoslovakia

[21] Appl. No.: 31,062

[22] Filed: Apr. 18, 1979

Related U.S. Application Data

[63] Continuation-in-part of Ser. No. 931,134, Aug. 4, 1978, abandoned, which is a continuation of Ser. No. 813,665, Jul. 7, 1977, abandoned.

[51] Int. Cl.³ .................... A61K 37/00; C07C 103/52
[52] U.S. Cl. .......................... 424/177; 260/112.5 R
[58] Field of Search ................ 424/177; 260/112.5 R

[56] References Cited

PUBLICATIONS

Torchiana, et al., Experimentia (1964) 24, pp. 570–571.
Kobayashi, et al., Bull. Chem. Soc. Japan 42, pp. 3491–3495 (1969).
Berde, Molecular Aspects 1968 pp. 53–65.

*Primary Examiner*—Delbert R. Phillips
*Attorney, Agent, or Firm*—Burgess, Ryan and Wayne

[57] ABSTRACT

The use of long-acting oxytocin analogs, characterized chemically by replacement of the disulfide bridge by a thioether bridge, in safely inducing labor in mammals is disclosed. Of particular importance in the use of these compounds is the safety factor, that is, the absence of uterine tetany, dangerous to both mother and fetus, at dosage levels required for induction of complete labor. Induction of complete labor can be accomplished with one or, at most, two single injections.

4 Claims, No Drawings

LONG-ACTING OXYTOCIN ANALOGS FOR USE IN INDUCING AND ACCELERATING LABOR IN MAMMALS, PARTICULARLY FARM ANIMALS

CROSS-REFERENCE TO RELATED APPLICATIONS

This application is a continuation-in-part of co-pending application Ser. No. 931,134, filed Aug. 4, 1978, which, in turn, is a continuation of application Ser. No. 813,665, filed July 7, 1977, both of which are now abandoned.

BACKGROUND OF THE INVENTION

This invention relates to a pharmacological means of inducing the entire physiological course of labor at an accelerated rate, or of accelerating labor in process, in mammals, particularly farm animals.

Controlled parturition in cattle has been a subject of veterinary investigation for over a dozen years. Aside from possible clinical reasons for inducing labor before its spontaneous onset, in large dairy herds, such a regimen could have economic significance if births could be planned or occur at manageable rates for the available personnel during their normal working hours. So far, three categories of substance have been tested for this purpose: steroids such as dexamethasone of flumethasone, prostaglandins and oxytocin.

Steroids can induce parturition within 72 hours of i.m. injection of doses around 20 mg/cow. Part of the mechanism of action involves a relaxation of the uterine cervix. There are, however, two specific difficulties: (1) a 72 hour period still does not allow one to predict whether the calf will be born during a given working day so that the newly born can be put by hand to sucking colostrum soon after birth which is associated with less post-natal disease than in calves born at night or on weekends and left without such care; (2) objections can be raised to the use of large steroid doses in general since residues are left in milk and meat for long periods. Prostaglandins have a much shorter biochemical half-life than steroids and their onset of action is more rapid, but there is a danger of putting the uterus into tetany, which endangers both the cow and the fetus.

Oxytocin (OT) in moderate dosage produces regular contractions of the pregnant uterus, but for very short periods of time after single doses and in addition vasoconstricts the blood supply to the uterus. Attempts to prolong the effect by giving excessive doses can result in uterine tetany or tachyphylaxis, both of which, as with prostaglandins, endanger the lives of mother and fetus. In human use, OT is given in continuous infusion at 1 ml/min of a solution of 20 IU/l.—which represents a rate of about 40 ng or pmol/min—in 5% glucose, but constant monitoring of uterine contractions and fetal heartbeat are required to prevent tetany and fetal damage. Reports of use in bovine obstetrics vary from a failure to induce labor with i.v. or i.m. injection of 100 IU (=about 0.2 mg.) to successful induction with i.v. infusion of only 4—5 IU over 1 hour (but in only 3 animals). A long-acting analog of OT could, thus, obviate such difficulties with tetany and tachyphylaxis, and in particular the practical impossibility of routine setting up of long term infusions in large animals, by accomplishing the desired effect with one or, at most, two, separate i.v. injections.

Thus, the natural hormone has a number of disadvantages: (a) the actions following separate injections are very short-lived, so that to induce labor in a cow it must be injected at 30-min. intervals, which is difficult and often impossible for the veterinary physician on practical grounds; (b) it can be used usually only after considerable dilation of the cervix has occurred; otherwise, particularly if larger doses are used in order to get sufficient duration of action, there is danger of uterine tetany which can endanger the life of both fetus and mother; and (c) natural oxytocin also produces vasoconstriction in the uterus, which is disadvantageous to the fetus (Goodman, L. S. & Gilman, A., Chapter on "Ocytocics" in "The Pharmacological Basis of Therapeutics". Macmillan Co., New York, 1965).

It would be of advantage to have an oxytocic drug which would, after one or, at most, two single injections, result in an oxytocic response starting within minutes of administration and lasting for several hours—of sufficient duration to cover the course of accelerated labor. Analogs of oxytocin have been described with a prolonged oxytocic activity such as 1-deamino-oxytocin, 1-deamino-1,6-dicarba-oxytocin and derivatives thereof (Kobayashi A., Hase S., Kiyoi R., Sakakibara S.: Bull. Chem. Soc. Japan 42:3491 (1969), Walter R., Yamanaka Y., Sakakibara S., Proc. Nat. Acad. Sci. U.S. 71:1901 (1974). Di-carba oxytocin analogs, however, in which both sulfur atoms have been replaced by methylene groups, although they have prolonged activity, shown such low potencies that very large doses would be required (Barth T., Krejci I., Kupkova B., Jost K., Europ. J. Pharmacol 24:183 (1973); Barth T., Krejci I., Vaneckova J., Jost K: Europ. J. Pharmacol. 25:67 (1974)).

There is also a relatively short-acting oxytocin analog—[2-Tyr(OMe)]-oxytocin, which, in comparision with the natural hormone, has one tenth the contractile activity on the myometrium, but its vasoconstrictor in the same organ is decreased to one hundreth (Hodr J., Stembera Z. K., Brotanek V., Rudinger J., Vondracek J.: The influence of methyl-oxytocin on glycide metabolism of mother and foetus, In "Intra-uterine Dangers to the Foetus", Excerpta Medica, Amsterdam, 1966, p. 445) so that if 10 times as much [2-Tyr(OMe)]-oxytocin as oxytocin itself (w/w) is administered, the same expulsive force from the uterus can be attained without a toxic, hypoxic effect on the fetus or induction of metabolic acidosis in the mother during labor. This short-acting analog is commercially produced and in clinical use (Methyloxytocin SPOFA) and its effectiveness has been demonstrated (Bartschi R., Huter J., Romer V. W., Geburtshilfe u. Frauenheilkunde 32:826 (1972)). Just as with oxytocin, induction of labor with this analog requires a continuous infusion and careful following of uterine contractions and cardiac action of the fetus in order to prevent damage to the latter.

In the sow, as in all other mammals, the biochemical half-life of injected oligopeptide hormones such as oxytocin is only a few minutes and the duration of the myometrial response to single injections is only slightly longer. As in other mammals, the sensitivity of the myometrium in the sow is increased under the influence of estrogen both in vitro and in vivo. While the duration of uterine response can be prolonged by giving large doses of oxytocin, one thereby runs the risk of uterine tetany (particularly during labor) and tachyphylaxis. Ideally the most physiological approach to prolonging oxytocin action until the required clinical task is accomplished would be to administer it by continuous i.v.

infusion as in human obstetrics. This is hardly possible under ordinary conditions of veterinary medical practice with large animals. One alternative solution would be a very long-acting analog of oxytocin so that single, or at most two separate, injections could cover several hours of pharmacological activity.

SUMMARY OF THE INVENTION

It is the primary object of the present invention to provide a method of inducing labor in mammals by administering a drug which, after application, would maintain its activity for a long period so that labor and delivery could be completed within a required time.

It is another object of the present invention to provide a method of increasing milk production in mammals by administering the drug described in the foregoing object.

DESCRIPTION OF THE PREFERRED EMBODIMENTS

Consistent with the foregoing objects, this invention is based on a long-acting structural analog of 1-deamino-oxytocin in which the disulfide bridge between residues 1 and 6 is replaced by a thioether one, as shown in the general formula I:

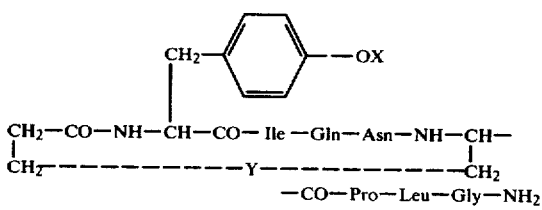

where $X=H$ or $CH_3$ and $Y=CH_2S$ or $SCH_2$. The dosage varies from 1 ng to 10 mcg/kg body wt. It has now been determined that the above substances can be used for:

(1) induction and completion of labor in women or in pregnant animals before the natural onset of labor, with a closed cervix, (2) acceleration of labor in women and animals after a physiological onset, but with slow progress, (3) accomplishment of (1) and (2) above wihout signs of uterine tetany or fetal anoxia, i.e., with an improved safety factor for both fetus and mother, and (4) facilitating milk production in dairy animals.

These analogs of 1-deamino-oxytocin were prepared by classical synthetic methods in solution (Jost. K., Collect. Czech. Chem. Commun. 36, 218 (1971); Jost K., Sorm F., ibid. 36:234 (1971); Rudinger J., Jost K., Czechoslovak Pat. No. 123,272 (PV 2429-61); Fric I., Kodicek M., Porchazka A., Jost K., Blaha K., Collect. Czech. Chem. Commun. 39:1290 (1974); Jost K., Barth T., Krejci I., Sorm F., Czechoslovak Pat. No. 149,028 (PV 1122-71)) and were available for experiments as freeze-dried powders. Chemical, physicochemical and pharmacological properties of some examples are listed in Table 1. All of these substances are easily soluble in water and solutions for injection were prepared containing 0.1 mg/ml normal saline, under sterile conditions, at pH about 4. Such solutions were kept at 5° C. until use.

TABLE 1

| Substance | Formula (m.w.) | Analysis (calculated/found) | | | Optical rotation (solvent) | K | $R_f$ TLC SBN/SBA | Biological activities (IU/mg) | | | | | |
|---|---|---|---|---|---|---|---|---|---|---|---|---|---|
| | | % C | % H | % N | | | | A | B | C | D | E | F |
| Ia $X=H, Y=CH_2S$ | $C_{44}H_{67}N_{11}O_{12}$ $S . 4H_2O$ (1046) | 50.52 50.42 | 7.23 6.62 | 14.73 14.61 | −71.7° (water) | 2.15 | 0.20 0.35 | 1899 | 1206 | 1127 | 581 | 604 | 24 |
| Ib $X=H, Y=SCH_2$ | $C_{44}H_{67}N_{11}O_{12}$ $S . H_2O$ (992) | 53.26 53.13 | 7.01 7.09 | 15.53 14.90 | −84.5° (1M $CH_3COOH$) | 1.95 | 0.20 0.35 | 922 | 2792 | 571 | 755 | 456 | 118 |
| Ic $X=CH_3, Y=CH_2S$ | $C_{45}H_{69}N_{11}O_{12}$ $S . 2H_2O$ (1024) | 52.78 52.29 | 7.18 6.90 | 15.05 14.88 | −69.0° (1M $CH_3COOH$) | 3.15 | 0.35 0.36 | 10 | 40 | — | 67 | 35 | 0.9 |

K = partition coefficient between 2-butanol and 0.05% acetic acid; SBN = 2-butanol, 25% ammonia, water (85:7.7:7.5); SBA = 2-butanol, 90% formic acid, water (75:13.5:11.5). A = isolated rat uterus, B = in situ rat uterus, C = vasodepression in the cock, D = isolated rat mammary gland, E = lactational activity in vivo (rat), F = antidiuretic in the rat. TLC = thin-layer chromatography.

Use of these substances has a number of advantages. Both for the health of the newborns and the cost in materials and time in care, it is advantageous to have a long-acting oxytocic effect which can rapidly initiate the entire process of labor and birth with an accelerated, physiological course with single injections of 5 mcg/kg body wt., without the danger of inducing uterine tetany and fetal anoxia which can complicate the use of other oxytocics for this purpose. In the case of calves it is important for their health that they get colostrum as a source of maternal immunoglobulins as soon as possible after birth. This requires personnel and is simpler to carry out if the calves are born in the daylight hours of a normal working day, which the substances referred to in this invention enable. The chemical basis of the claimed activities are based on (a) the absence of an $N^{alpha}$-amino group of 1-cysteine which prevents aminopeptidase cleavage of the molecule into inactivity, (b) replacement of the disulfide bridge by a thioether one, which eliminates disulfidase cleavage of the molecule into inactivity and (c) if desired, replacement of the p-OH group of 2-tyrosine by a methoxy group. With the prolonged activity thus produced, labor can be induced early in the morning on a working day and birth can take place in the afternoon of the same day when combined with dexamethasone or prostaglandin pre-treatment, or with injection the evening before and birth the next working day if used without any other pre-treatment. This can be used several days to one week before the expected onset of spontaneous labor. In swine, labor is prolonged with large litters and frequently the last piglets to be born are anoxic and either die or the mother kills them. Compounds used in the present invention, in the same dosage also cause prolonged, rhythmic contractions of the sow's uterus with no signs of tetany, and so can be used to accelerate labor and increase the percentage of viable, healthy young. The preferred range of dosage is from about 10 ng to about 100 μg. per Kg. of body weight. A more preferred range is from about 1 μg to about 10 μg per Kg. The substance is administered in solution in any carriers such as saline or water.

EXAMPLE 1

250–300 g body wt female rats (n=5 for each substance) were pre-treated for 3 days with 50 mcg diethylstilbestrol and 25 mg progesterone injected once daily i.m. in order to fully "estrogenize" the animals and have them all in the sam functional state of myometrial reactivity. They were then anesthetized with urethane and prepared for in situ measurements of uterine horn contractions using Grass force-displacement transducers and polygraph recording. Table 2 shows that equipotent doses of 1-deamino-1-monocarba-[2-Tyr(OMe)]-oxytocin,1-desamino-oxytocin,[2-Tyr(OMe)]-ocytocin, B = (numbers) = contraction frequency per 10 min. in % increase.
C = duration of the response in minutes and
D = the presence of tetany in % of the animal group, as defined by a single maximal contraction lasting more than 10 min. All numbers as means ± SEM, except for D.

EXAMPLE 2

These experiments were carried out on 13 pregnant 'Czech red-spotted' cows ranging from para I to para V. Average pregnancy in this breed is 290 days in duration.

Nine of the animals were 278–290 days after insemination but actual active labor had not yet begun. These animals received no other medication (Table 3).

TABLE 3

| | | | | | Group I - effect of dCOMOT in non-treated cows. | | | | | |
|---|---|---|---|---|---|---|---|---|---|---|
| No. | Age years | Para | dCOMOT 1st | dose 2nd | Duration of Labor hrs. | Day of pregnancy (from insemination) | Progeny Sex | Body wt(kg) | Serum pH | Placenta delivery |
| 1 | 3 | II | 5 | — | 26 | 287 | M | 51 | 7.4 | — |
| 2 | 4 | II | 5 | — | 34 | 287 | F | 42 | 7.4 | — |
| 3 | 5 | IV | 5 | — | 22.5 | 290 | M | 51 | 7.4 | + |
| 4 | 6 | V | 5 | — | 6 | 286 | F | 40 | 7.4 | — |
| 5 | 5 | IV | 5 | — | 24.5 | 278 | M | 45 | 7.3 | — |
| 6 | 3 | II | 5 | — | 10 | 281 | F | 43 | 7.4 | + |
| 7 | 2 | I | 5 | — | 1.5 | 288 | M | 45 | 7.4 | + |
| 8 | 2 | I | 5 | — | 7 | 290 | F | 39 | 7.3 | — |
| 9 | 5 | IV | 3 | 2.5 | 15 | 287 | F | 45 | 7.4 | — |

TABLE 4

| | | | | | Group II - effect of dCOMOT in pretreated cows. | | | | | |
|---|---|---|---|---|---|---|---|---|---|---|
| No. | Age years | Para | dCOMOT 1st | dose 2nd | Duration of Labor hrs. | Day of pregnancy (from insemination) | Progeny Sex | Body wt(kg) | Serum pH | Placenta delivery |
| 1 | 4 | II | 5 | — | 0.7 | 280 | M | 44 | 7.4 | — |
| 2 | 3 | I | 5 | — | 8.2 | 273 | F | 40 | 7.4 | — |
| 3 | 4 | II | 5 | 2.5(7 h) | 8.8 | 280 | F | 48 | 7.4 | — |
| 4 | 3 | I | 5 | — | 8.6 | 275 | F | 35 | 7.4 | — | and oxytocin itself, all in doses comparable to those used to induce labor in cows in Example 2 with the first of the three substances named/above, gave the following results: (1) the longest duration of oxytocic action was associated with the monocarba analog, followed, by the other substances in the order given above. (2) while neither of the two [2-Tyr(OMe)] substituted analogs showed any incidence of uterine tetany, long-acting 1-deamino-oxytocin and short-acting oxytocin both gave high incidences of uterine tetany in the equipotent doses used.

TABLE 2

| Substance (dose) | A | B | C | D |
|---|---|---|---|---|
| 1-deam . monocarba-[2-Tyr(Ome)]-OT (10 mcg/kg iv.) (d COMOT) | 65 ±6.3 | (60 ± 5.3) | 185 ±18 | none |
| 1-deamino-OT (1 mcg/kg iv.) (d OT) | 92 ±6.5 | (65 ± 6.2) | 46 ±6.3 | 60 |
| [2-Tyr(OMe)]-OT (10 mcg/kg i.v.) (Me-OT) | 68 ±7.4 | (42 ± 5.4) | 20.6 ±2.3 | none |
| oxytocin (OT) (1 mcg/kg iv.) | 90 ±4.2 | (43 ± 3.2) | 10.4 ±2.6 | 60 | where
A = amplitude of contractions as a % of maximal contraction induced by a tetanic dose of 10 mcg/kg oxytocin at the end of the experiment in each animal, Four of the animals were estimated to be near to term (cf. Table 4). 48 hours before the actual experiment they received 20 mg dexamethasone i.m. in an attempt to prepare the uterine cervix for active labor. In this group, in addition to close clinical follow-up, measurements were also made of: body temp., hemoglobin (Hb), glucose, total protein, inorganic P, Ca and Mg concentrations in the blood, both in the cow during the experiment and in the calf after birth, all by standard methods.

The standard i.v. (jugular) injection dosage of dCOMOT was 5 mg. In those cases in which labor lasted longer than 6 hours (cf. Results) a second injection was given.

The first group of 9 cows was managed under field conditions—in the barns of local farms. The four animals under more intensive study were kept in stalls set aside in a research building for one week prior to the onset of the experiment and for 3 weeks following delivery for further postnatal observations.

Group I - 9 non-pretreated cows.

All the animals were in the range of term pregnancy—278–290 days from insemination (means 286±2.0 SEM) (Table 2)—and clinically their status corresponded well: loosening of pelvic joints and connective tissue, edematous and dilated state of the vagina and vulva and filled state of the udders. Vaginal and rectal examination showed, however, that in no case were there regular uterine contractions related to the onset of labor and the fetal membranes were intact. The mean width of the external os at the start of the experiment was 5±1.4 cm, range 2–10 cm).

In all cases, injection of dCOMOT was followed by the onset of regular uterine contractions and increased tension in the udder (with milk ejection either at rest or during Valsalva "bearing down"). Of great interest was the fact that the course of the induced labor was highly physiological—the rate of contractions started at about 1/10–15 min and slowly accelerated, while the intensity of the contractions apparently also increased with time. There was no evidence of uterine tetany whatsoever. In the most dilated cow (10 cm external os at the time of dCOMOT injection), delivery was complete 1.5 hours after injection. All the calves were healthy and continued to develop normally in the post-natal period. Mean duration of labor was 14.25±5.1 (SEM) hours from the dCOMOT injection.

Group II - 4 dexamethasone pretreated cows.

This group ranged in duration of pregnancy from 273 to 280 days (mean 277±1.8)—somewhat further from term than Group I. In all cases the external os was closed when, 48 hours before dCOMOT injection, they received 20 mg dexamethasone i.m. At the time of dCOMOT injection, the external os ranged from 4 to 10 cm, mean 6±1.5. In all cases, as above, active labor started within minutes of dCOMOT injection, not before. The mean duration of labor was only 4.3±2.1 hours, range 1.52 (external os 10 cm at injection) to 8–9 hours.

As in Group I, here as well, all calves were healthy and remained so postnatally, showing no signs of hypoxia at birth. In no cases was uterine tetany observed during the induced labor.

The sensitivity of the myometrium to OT is fairly low in the non-pregnant uterus (in comparison with vasopressin, for example) and for the first third of pregnancy. Sensitivity increases rapidly as term approaches, and so is clearly a function of myometrial changes induced, among other things, by increasing levels of secreted steroids. As pointed out earlier, attempts at prolonging OT action by increasing dosage carry with them the danger of producing either uterine tetany or tachyphylaxis or both sequentially. Such a result is extremely dangerous for both mother and fetus. Of great practical and perhaps theorectical interest in the present work and other related observations is that a long-acting OT such as dCOMOT has not yet shown any signs of producing tetany or tachyphylaxis despite large doses.

Combination of dCOMOT with dexamethasone clearly gave the best results since the shortest times for all stages of the labor were recorded in Group II. It would appear that using such a combination, injection of dCOMOT at, say, 5:00 AM would result in the birth of a healthy calf within the same 8-hour work shift on the same day. Were dCOMOT to be used alone so as to avoid steroids, the peptide would have to be given the afternoon before the day of delivery.

EXAMPLE 3

Experiment I - in vitro in sows

The stage of the estrus cycle was determined at the slaughter house by the appearance of the ovaries-at estrus the latter contain large follicles (8–10 mm) combined with small corpora lutea (3–4 mm). The reproductive organs were removed from four sexually mature females in heat within a few minutes of sacrificing and were rapidly transported to nearby laboratories. A number of strips 20×4 mm were cut longitudinally from the uterine horns suspended in Tyrode solution at 5° C. The strips were then mounted in 40 ml cuvettes in isolated organ baths. The bath fluid (Tyrode/solution bubbled through with 5% $CO_2$ in $O_2$) circulated continuously from below at a constant rate of 1 ml/min and was maintained at a temp of 37° C. by a thermostat. Contractions were recorded by a force-displacement transducer (Grass FTOC3) connected to a Polygraph (Model 79C, Grass Instrument Co., Quincy, Mass.). It took about 2 hours as a rule for the strips to reach a balanced baseline state of activity. Only after the latter had been attained were the following substances added to the medium alternately, in increasing dosage: synthetic oxytocin (OT) (Partocon[R]—Ferring, Malmo, 10 IU/ml) and 1-desamino-1-monocarba-[2-Tyr(OMe)]-OT (dCOMOT) (substance supplied by Drs. K. Jost and J. H. Cort, ampuled by Ferring at 0.2 mg/ml physiological saline, pH about 4).

Spontaneous activity and responses to OT and dCOMOT were determined. The baseline contraction rate was 6–8/10 min. All strips responded to OT, initially with an increase in baseline tone and thereafter an increase in contraction rate. Duration and intensity of response varied between strips independently of dosage (2.5–25 mIU/ml medium) (the equivalent of 5–50 ng OT/ml) with duration varying from 15 to 40 min.

dCOMOT medium concentrations were varied from 500 to 5000 ng/ml and the pronounced responses ranged from 30 to 120 min without relation to the above concentration range. The response was more related to an increase in contraction rate than to an increase in baseline tone. It was noted that there was a tendency to waves of response during the prolonged effects of dCOMOT. Despite the large doses used, the strips did not go into tetany.

Experiment II - in vivo in sows

Four gilts were used. The experiments started about 24 hours after onset of their second or third estrus. Their cycle duration was in the range 19–22 days. They were anesthetized by i.v. administration of about 15 mg/kg Na thionembutal (in 5% (w/v) solution)—additional doses were required during the experiment.

The uterus was exposed through a midline abdominal incision. A recording balloon-tipped catheter was inserted into each uterine horn through a small incision about 10 cm from the uterine body (Clay-Adams catheters, PE 90–0.86 mm i.d. × 1.27 mm o.d., with a microballoon sealed over the tip with a double tie of 0000 silk suture). The recording system was filled with saline and each catheter was affixed to the uterine wall with 000 silk suture to prevent motion of the balloon in the lumen. The catheters exited through the mid-abdominal incision and were connected to P-23AC pressure transducers, thence to 7PL DC preamplifiers. When we were satisfied that the recording system was functioning the abdominal incision was closed about the catheters.

Spontaneous uterine activity was recorded for at least one hour, usually two hours, before test substances were administered (OT and dCOMOT as above) i.v.

In both experiments, since orientation results only were sought and limited amounts of dCOMOT were available, a dCOMOT:OT ratio of 100 was used as a more judicious investment of drug in a large animal should the lower ratio prove ineffective. Unfortunately, there was not enough material for a full scale dose-response investigation.

The baseline contraction rate was 6/10 min. OT was given i.v. in doses of 1 to 5 IU (equivalent to 2-10 ug). The response to OT involved initially a small increase in tone followed by an increase in contraction rate from 6/10 to 8/10 min. In one case this was also accompanied by an increase in contraction amplitude. Over the dosage range given, response duration was approximately 10 min. dCOMOT was injected in the dose range 0.2 to 1.0 mg. The responses ranged from 60 to 120 min in duration between gilts. However, there was no significant dose response in the dose range used. Initially, a small 2 min. increase in tone was demonstrated. Thereafter the most pronounced aspect of the response was the increased contraction rate (from 6/10 to 8-10/10 min). Again there were waves of reaction seen after dCOMOT injection, but no tetany despite the large dose.

What is claimed is:

1. A method for inducing tetany-free labor in mammals which comprises administering an effective amount of a compound of the formula

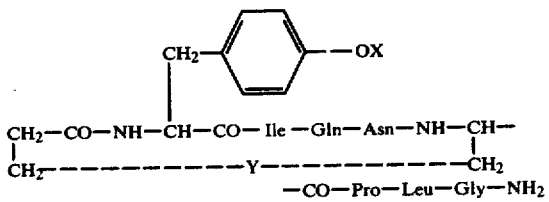

where X is H or $CH_3$ and Y is $CH_2S$ or $SCH_2$.

2. A method according to claim 1, wherein said effective amount varies between about 10 ng and about 100 μg/kg of the body weight of the mammal.

3. A method according to claim 2, wherein said effective amount is from about 1 μg to about 10 μg per Kg.

4. A method according to claim 1, comprising administering said compound by injection as a solution in a pharmaceutically acceptable carrier.

* * * * *